United States Patent [19]

Bookspan

[11] Patent Number: 5,086,781
[45] Date of Patent: Feb. 11, 1992

[54] BIOELECTRIC APPARATUS FOR MONITORING BODY FLUID COMPARTMENTS

[76] Inventor: Mark A. Bookspan, 1328 de la Guerra Rd., Santa Barbara, Calif. 93103

[21] Appl. No.: 436,476

[22] Filed: Nov. 14, 1989

[51] Int. Cl.$^5$ .............................................. A61B 5/05
[52] U.S. Cl. ................................. 128/734; 128/774; 128/783; 128/804
[58] Field of Search ............... 128/734, 774, 783, 795, 128/796, 804

[56] References Cited

U.S. PATENT DOCUMENTS

| | | | |
|---|---|---|---|
| 2,660,717 | 11/1953 | Hood | 340/255 |
| 2,816,264 | 12/1957 | Hood | 324/62 |
| 2,827,041 | 3/1958 | Pierson | 128/2.1 |
| 3,085,566 | 4/1963 | Tolles | 128/2.1 |
| 3,316,896 | 5/1967 | Thomasset | 128/2.1 |
| 3,340,867 | 9/1967 | Kubicek et al. | 128/2.05 |
| 3,347,223 | 10/1967 | Pacela | 128/2.1 |
| 3,452,743 | 7/1969 | Rieke | 128/2.1 |
| 3,730,171 | 5/1973 | Namon | 128/2.05 Z |
| 3,735,247 | 5/1973 | Harker | 324/34 R |
| 3,742,936 | 7/1973 | Blanie et al. | 128/2.1 Z |
| 3,750,649 | 8/1973 | Severinghaus | 128/2.1 Z |
| 3,784,908 | 1/1974 | Anderson | 324/62 |
| 3,789,834 | 2/1974 | Duroux | 128/2.1 Z |
| 3,851,641 | 12/1974 | Toole et al. | 128/2.1 Z |
| 3,949,736 | 4/1976 | Vrana et al. | 128/2.1 Z |
| 3,971,365 | 7/1976 | Smith | 128/2.1 Z |
| 4,008,712 | 2/1977 | Nyboer | 128/2.1 Z |
| 4,116,231 | 9/1978 | Matsuo | 128/2.1 Z |
| 4,155,351 | 5/1979 | Teshirfea et al. | 128/734 |
| 4,263,920 | 4/1981 | Tasto et al. | 128/734 |
| 4,408,282 | 10/1983 | Hof | 364/482 |
| 4,947,862 | 8/1990 | Kelly | 128/734 |

OTHER PUBLICATIONS

"Electrical Measurement of Fluid Distribution in Legs and Arms" by Kanai et al., Med. Prog. Technol., 1987, 12 (3-4) pp. 154-170.
Kanai et al., Electrical Measurement of Fluid Distribution in Human Legs: Estimation of Extra- and Intra-Cellular Fluid Volume, Journal of Microwave Power, 18 (3) p. 233, (1983).
Meijer et al., Measurement of Transcellular Fluid Shift During Haemodialysis, Med. & Biol. Eng. & Comput. 27, pp. 147-151 (1989).
de Vries et al., Measurement of Transcellular Fluid Shift During Haemodialysis, Med. & Biol. Eng. & Comput. pp. 152-155 (1989).

Primary Examiner—David Shay
Attorney, Agent, or Firm—Kenneth W. Float

[57] ABSTRACT

Apparatus for monitoring body water compartmentalization, specifically intracellular and extracellular body water. The apparatus includes a signal generator for generating a sequence of constant current electrical signals at a predetermined number of frequencies ranging between 1 kHz and 2 MHz. Bioelectric contacts are applied to the subject at two sets of points. The resistance drop across the subject is measured by a resistance measuring circuit using one set of contacts. The phase shift between the signals sensed by the sets of contacts is measured by a phase detecting circuit. The current produced by the signal generator is monitored and regulated to maintain the signals at a constant current. The measured data are combined with anthropometric data entered by means of a keyboard, a scale, or other input device, and processed by means of a microprocessor. The micropressor computes a subject's extracellular, intracellular and total body water as a function of the bioelectric and anthropometric data.

21 Claims, 3 Drawing Sheets

BIOELECTRIC APPARATUS FOR MONITORING BODY FLUID COMPARTMENTS

BACKGROUND

The present invention relates to devices for measuring and/or monitoring body fluid compartmentalization and in particular to devices that utilize multiple frequencies and body impedance and/or resistance and/or capacitive reactance measurements to determine body water volume and the intracellular versus extracellular water distribution.

The body's water content and its distribution between intracellular and extracellular compartments are biologically and pathologically significant and an accurate determination thereof can be used to improve medical care. The present derivation of these parameters has been made using laboratory measurement techniques commonly referred to as the "gold standard". Due to the time and expense involved in effecting such measurements, the measurements are not routinely made, and valuable diagnostic information is frequently not available to the physician.

For example, while heart failure is diagnosed and treated properly in the majority of patients, there are patients who are not properly diagnosed. These patients include those who show early signs of myocardial dysfunction, but do not exhibit tell-tale clues, and consequently, treatment is withheld. Others include symptomatic patients whose condition is incorrectly diagnosed as heart failure. Similar errors in diagnosis apply to disorders usually characterized by hypovolemia or total body water loss. Again, because of the known difficulty in accurately assessing a patient's hemodynamic and fluid status by physical examination alone, physicians rely on a number of calculations and special studies to assist in their diagnosis. These aids include frequent sampling of serum and urine for determination of osmolality, electrolyte concentration, and renal function studies, and placement of indwelling balloon-tipped catheters in a patient's pulmonary artery. Measurements obtained with such catheters may influence therapy, but in some cases the catheters produce serious complications in the patient. Such procedures are still of unproven utility in improving overall patient morbidity and mortality and are fraught with difficulties in interpretation.

In the medical literature, there is sufficient information to show that bioelectrical impedance determination can provide useful information in patient diagnoses. There is little doubt that in healthy individuals, single-frequency bioelectric impedance determinations correlate closely with total body water stores. However, there is a problem with reliability and accuracy when this method is used to evaluate body water stores in individuals who are not healthy. These problems are caused by applying data from healthy individuals to the evaluation of individuals having disorders involving water homeostasis, when one of the underlying assumptions made in the study of healthy individuals no longer holds true. Specifically, healthy individuals have a constant relationship between total body water and extracellular water. Individuals with diseases such as heart disease, renal disease, liver disease, malnutrition, and severe dehydration have an unpredictable ratio of total body water to extracellular water.

In prior attempts to measure water compartmentalization, researchers have noted a frequency dependent variation in tissue impedance. Reference is made to U.S. Pat. No. 3,316,896, entitled "Apparatus and Methods for the Measure of the Electrical Impedance of Living Organisms," issued to Thomasset, U.S. Pat. No. 3,949,736 entitled "Circuit for Automatically Deriving and Measuring Relative Voltages Associated with Impedance Components of a Biological Object," issued to Vrana et al., U.S. Pat. No. 3,971,365 entitled "Bioelectrical Impedance Measuring System," issued to Smith, and U.S. Pat. No. 4,155,351 entitled "Medical Instrument for Detecting Body Impedance," issued to Teshima et al., which disclose information regarding the frequency dependent variation in tissue impedance.

In a given tissue, the magnitude of the frequency-dependent impedance change correlates with the ratio of extracellular water to total water. Prior investigators suggest that the total water measurement is best predicted at low frequencies, but our studies show that low frequency measurements largely ignore the intracellular water and, thus, are accurate only when the intracellular to extracellular water ratio is constant. Previous efforts have been made to establish a relationship between a subject's frequency-related bioelectric impedance, measured total body water and intracellular or extracellular water. To date, these efforts have failed to obtain mathematical correlations sufficiently good for use in clinical medicine. However, these efforts have produced results sufficient to establish rough guidelines and to indicate predictive differences in health and disease. At the present time, published equations for determining the compartmentalization of body water have not been fully developed.

Conventional approaches employed in determining the water content of the body as well as its intracellular and extracellular water distribution are described in U.S. Pat. No. 4,008,712, entitled "Method of Monitoring Body Characteristics," issued to Nyboer, an article entitled "Measurement of Transcellular Fluid Shift During Haemodialysis," by Meijer et al., in *Medical & Biological Engineering & Computing*, page 147, March 1989, and in "Electrical Measurement of Fluid Distribution in Human Legs: Estimation of Extra- and Intra-Cellular Fluid Volume," by Kanai et al., in *Journal of Microwave Power*, Vol. 18, No. 3, page 233 (1983).

The Kanai et al. article illustrates a system that is adapted to monitor relative shifts in body fluids, which system is shown in FIG. 6 thereof. Kanai et al. describe measurements of water compartment shifts, in relative terms, monitored in the frequency range of 1-100 KHz. Very little is described regarding the specifics of the circuitry employed to monitor body impedance.

Accordingly, there exists a need for a system that accurately and repeatably measures body impedance over a range of frequencies and combines this information with anthropometric data and empirically derived relationships to provide clinically usable data for monitoring body water volume and compartmentalization in both absolute and relative terms.

SUMMARY OF THE INVENTION

Broadly, the invention is a system that measures body water compartmentalization of a human subject. The system includes circuitry for measuring body impedance between predetermined points of a subject, and at a plurality of predetermined frequencies typically ranging between 1000 Hz and 2 Mhz. Signal generating circuitry is also provided for generating the signals having a plurality of frequencies between 1000 Hz and 2 Mhz. Means are provided to enter tissue or serum electrolyte concentration data, anthropometric parameters of a subject, including total body weight, height, arm span, and parameters relating to skeletal size, including wrist circumference, for example. A computing circuit is employed to process the measured impedance, resistance, phase angle, capacitive reactance, and electrolyte data and anthropometric parameters, to compute the intracellular, extracellular and total water volumes as functions thereof, in accordance with empirical relationships derived from measurements on a number of subjects.

In a specific embodiment of the invention, the impedance measuring circuitry includes a signal generator and amplifier for applying a constant magnitude alternating current to a subject at the plurality of frequencies by way of a first pair of electrodes. A second pair of electrodes is positioned between the first pair of electrodes and is connected to a resistance measuring device. The phase shift between the applied signal and the signal derived from the subject is combined with a resistance measurement to determine the subject's body impedance at each of the frequencies. Typically, the anthropometric and electrolyte data are entered into the system by means of a keyboard. The subject's weight is entered by way of the keyboard or input directly from an electronic scale which is connected to the computing circuit. Appropriate output devices such as a display or printer are included. Isolation and high frequency circuitry may be incorporated into the electrode assembly to eliminate measurement errors that are caused by connecting cable capacitance.

It is therefore a feature of the invention to provide a system for measuring and/or monitoring body water compartmentalization in absolute as well as relative terms. Another feature is to provide a system that determines body water compartmentalization as a function of frequency dependent impedance and/or resistance, and/or capacitive reactance of a subject. Still another feature is to provide a system in which anthropometric and tissue or serum electrolyte concentration data relating to a subject are incorporated with the subject's impedance data into an empirically derived equation to determine body water compartmentalization. Another feature is to provide a system that utilizes a low voltage, alternating current signal as a measuring signal in conjunction with a plurality of electrodes connected to a subject, to measure the resistance and phase shift of the applied signal, and wherein the measuring signal current is regulated and maintained at a constant level. Another feature is to provide a system that uses a microprocessor to automatically apply alternating current voltages at a sequence of frequencies to the subject and accumulate measured resistance and phase shift information in conjunction with tissue or serum electrolyte concentration and anthropometric data and automatically compute body water compartmentalization data. Yet another feature is to provide a system that is substantially automatic in operation, simple to use, and that provides clinically reliable information useful in monitoring body water compartmentalization.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
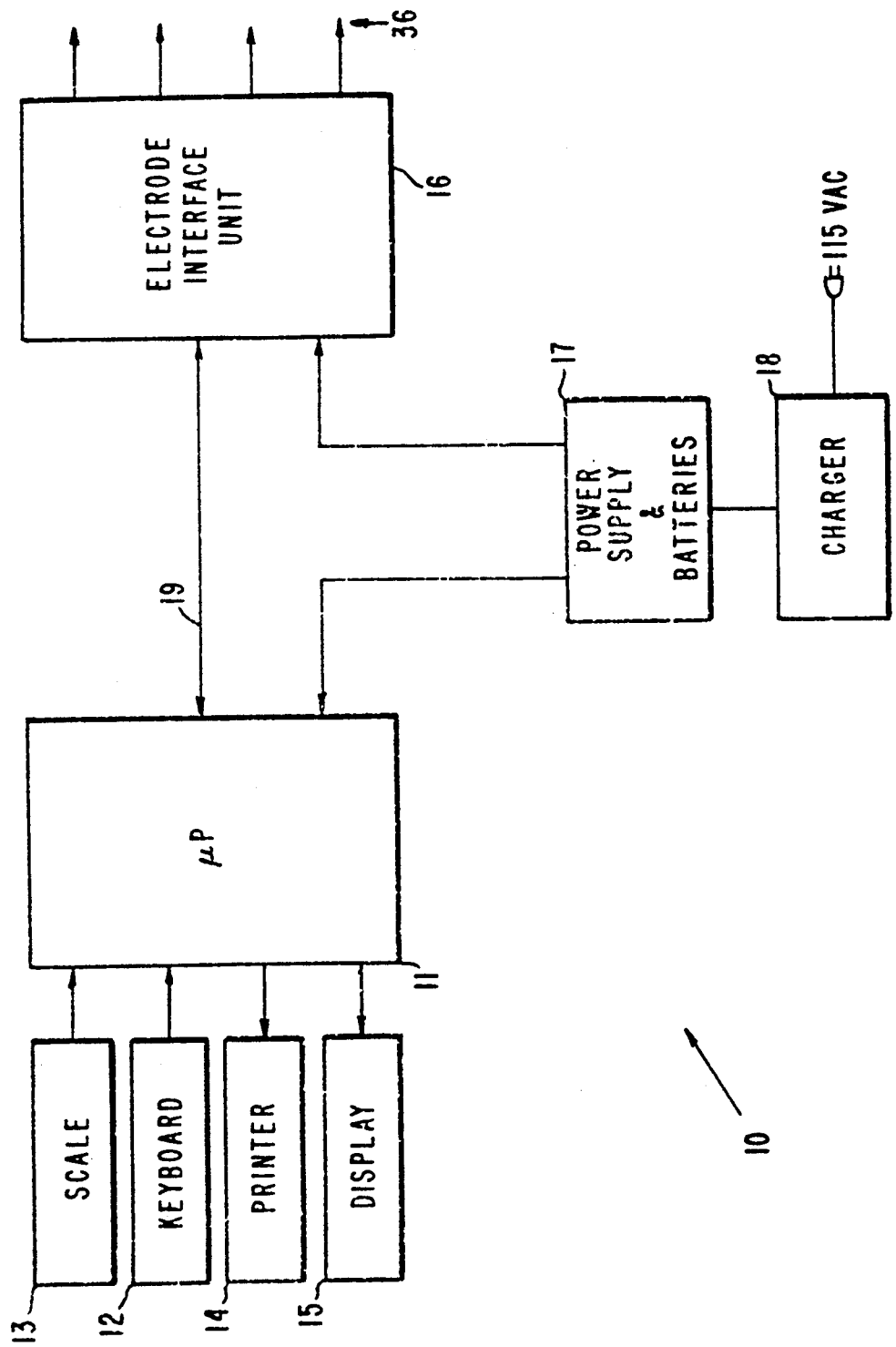
FIG. 1 is a block diagram of a system for measuring body water compartmentalization in accordance with the present invention.

Referring now to FIG. 1, there is shown a block diagram of a system 10 in accordance with the principles of the present invention for measuring and monitoring body water compartmentalization. The system 10 includes a control unit 11, or computer, to which is coupled a keyboard 12, an electronic scale 13, a printer 14 and a display 15. The printer 14 and display 15 are representative of various output means which may be employed to display computed information. An electrode interface unit 16 is connected to the control unit 11 by means of a communications link 19. Also connected to the control unit 11 and electrode interface unit 16 is a battery operated power supply 17 that includes a battery recharger 18. The electrode interface unit 16 is battery operated for patient safety and the recharger 18 is disconnected during operation The keyboard 12 is adapted to permit input of anthropometric data relating to a subject. Patient weight, comprising digital weight data, is coupled to the control unit 11 from the scale 13 for use in computation. Computed data is displayed to a physician or operator by means of the printer 14 and the display 15, respectively.

Figure 2:
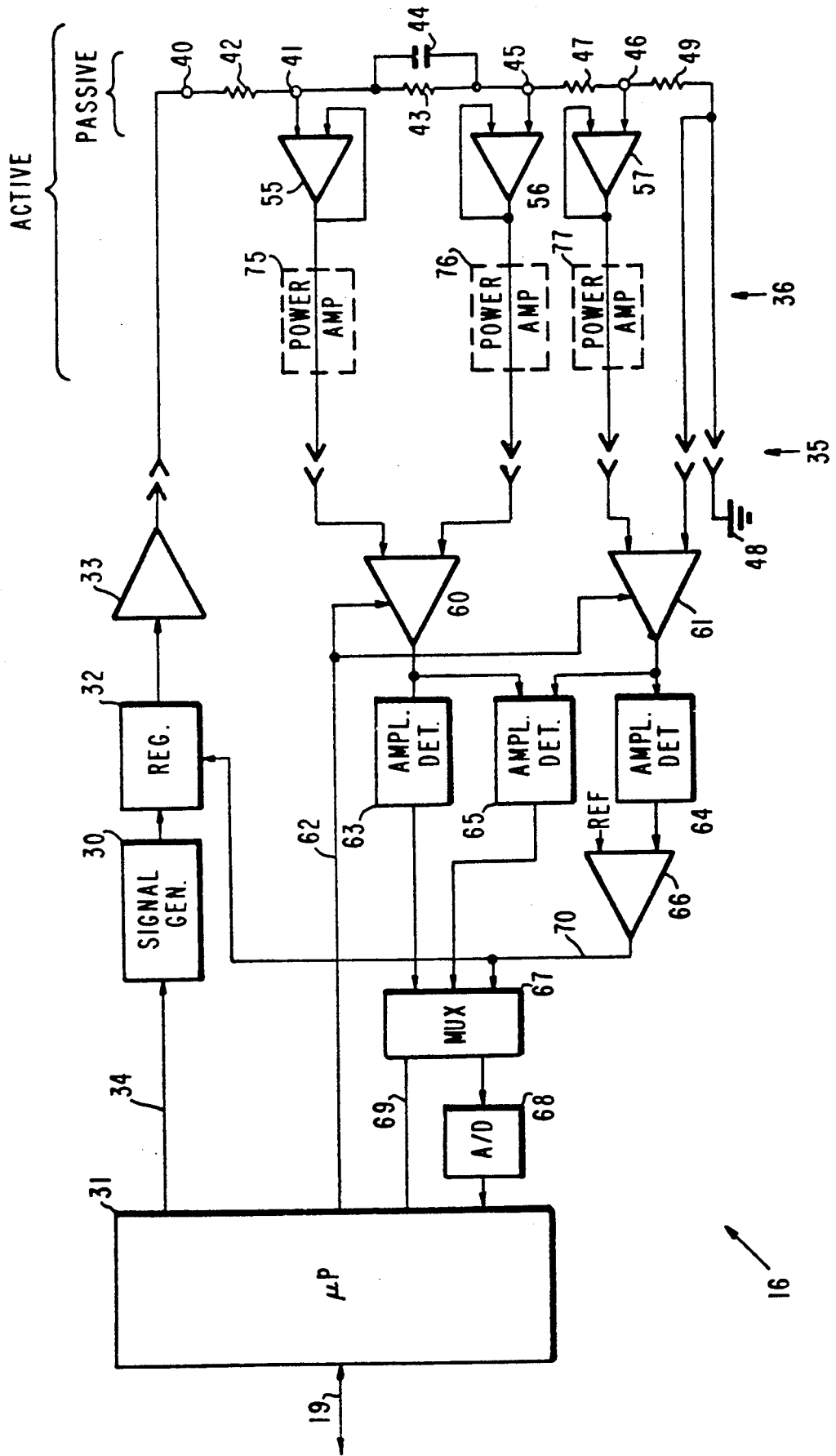
FIG. 2 is a detailed diagram showing the electrode interface unit of FIG. 1.

Referring to FIG. 2, it shows a detailed illustration of the electrode interface unit 16 of FIG. 1, and the electrode connections that are coupled to a human subject (not shown). The electrode interface unit 16 includes a signal generator 30, which may be a sine wave oscillator, such as may be configured using commercially available devices having model numbers LT1016, LM318 or CA3086, for example. The signal generator 30 is adapted to produce an alternating current sine wave signal at a selected one of a plurality of frequencies, including 1 kHz, 2 kHz, 10 kHz, 20 kHz, 50 kHz, 100 kHz, 200 kHz, 500 kHz, 1 mHz and 2 mHz, for example. The frequencies are automatically selectable by means of a microprocessor 31, which may be an Intel model 8039 processor, for example, that is adapted to provide an appropriate binary code to switch the signal generator 30 by way of a frequency select line 34. Alternatively, the frequencies may be switch selectable.

An output from the signal generator 30 is coupled by way of a regulator circuit 32 to a power amplifier 33. The regulator circuit 32 may be a model AD539, while the power amplifier 33 may be a model EL2020, for example. The output from the power amplifier 33 is coupled by means of one of a plurality of terminals 35 and cables 36 to one electrode of a first pair of conventional bioelectric contacts or electrodes 40, 41. The first pair of electrodes 40, 41 is applied to appropriate points on the subject (not shown). The first pair of electrodes 40, 41 is conventional metallic discs well known in the art. The contact resistance, or body resistance, between the first pair of electrodes 40, 41 is represented by a first resistor 42. Body impedance is represented by a second resistor 43 and capacitor 44 disposed in parallel therewith, which impedance is in series with the contact resistance represented by the first resistor 42.

A second pair of bioelectric contacts or electrodes 45, 46 that is substantially identical to the first pair of electrodes 40, 41 is applied to the subject at a location that is physically between the first pair of electrodes 40, 41, although not shown as such in FIG. 2. As with the first pair of electrodes 40, 41, the contact resistance between the second pair of electrodes 45, 46 is represented by a third resistor 47. A current monitoring resistor 49 is connected between one electrode 46 of the second pair of electrodes 45, 46, and ground 48. Three of the electrodes 41, 45, 46 are isolated from the system 10 by means of three isolation amplifiers 55, 56, 57, which may comprise model LM310 amplifiers, for example.

The two pairs of electrodes 40, 41, 45, 46 and the three isolation amplifiers 55, 56, 57 are remotely located from the electrode interface unit 16. They are separated from the electrode interface unit 16 by the cables 36. As shown in FIG. 2, the electronics related to the electrodes 40, 41, 45, 46 are passive. However, it is also contemplated by the present invention to employ an active electrode configuration which includes the isolation amplifiers 55, 56, 57 and power amplifiers 75, 76, 77 in the electrodes 40, 41, 45, 46 to minimize high frequency capacitance effects above about 200 KHz. This is illustrated in FIG. 2 by the power amplifiers 75, 76, 77 shown in dashed lines therein. The components comprising the active and passive embodiments are also indicated by bracketed and labeled portions of FIG. 2.

Outputs of two of the isolation amplifiers 55, 56 from the electrode portion of the system 10 are coupled to inputs of a first instrumentation amplifier 60 located in the electrode interface unit 16. The first instrumentation amplifier 60 is a constant gain amplifier, such as is provided by a model EL2020 amplifier, for example. Optionally, the gain of the first instrumentation amplifier 60 may be automatically controlled at one or more values by the microprocessor 31 by means of an optional gain control line 62. An output from the first instrumentation amplifier 60 is coupled to a first amplitude detector 63, which may be comprised of a model EL202 and IN5711 devices, for example, and the output of this detector 63 is coupled by way of a multiplexer 67 to an analog to digital converter 68. The multiplexer 67 may be a model DG508, while the analog to digital converter 68 may be a model AD574, for example. The analog to digital converter 68 is coupled to the microprocessor 31 for use in computing body water compartmentalization.

The current monitoring resistor 49 is coupled through the third isolation amplifier 57 to a second instrumentation amplifier 61, which may be a model EL2020 amplifier, for example. The voltage drop across the current monitoring resistor 49 is applied to one input of the second instrumentation amplifier 61. The gain of the second instrumentation amplifier 61 is optionally controlled by the microprocessor 31 by way of the gain control line 62. An output from the second instrumentation amplifier 61 is coupled by way of a second amplitude detector 64, to a first input of an integrator 66 which has a second input connected to receive a reference signal from a reference signal source (not shown). The second amplitude detector 64 may also be comprised of a model EL202 and IN5711 devices, for example. The differential inputs from the amplitude detector 64 and reference source are adapted to be integrated to provide a current regulating signal which is coupled by way of a feedback line 70 to the regulator 32, and is adapted to regulate the output of the signal generator 30 and maintain a constant current signal at each of the frequencies.

The outputs from the first and second instrumentation amplifiers 60, 61 are also coupled to inputs of a phase detector 65. The phase detector 65 may be a model NE521 integrated circuit, for example. The phase detector 65 is adapted to detect the phase shift of the signals passing through the subject which occur between the pairs of electrodes 40, 41, 45, 46. The phase detector 65 provides a signal that is coupled through the multiplexer 67 to the analog to digital converter 68 and then to the microprocessor 31 for computation therein. The output from the integrator 66 is also coupled through the multiplexer 67 and the analog to digital converter 68 to the microprocessor 31 to provide a current magnitude signal for computation therein. Addressing and sequencing of the multiplexer 67 is effected by multiplexer address lines 69 coupled from the microprocessor 31. Data generated within the microprocessor 31 is coupled to the control unit 11 by means of the conventional digital communications link 19.

The system 10 has a tetrapolar design wherein the first (outer) pair of electrodes 40, 41 generate an alternating constant current measuring signal across the first set of electrodes 40, 41 on the subject. The second (inner) pair of electrodes 45, 46 monitors the waveform and the voltage drop across the first pair of electrodes 40, 41. The applied current remains constant, but the frequency of the applied signal is varied across the frequency range. The typical resistance measuring range is from 150–2000 ohms, and a measurement accuracy of $\pm 1$ ohm is achieved. It will be recognized by those skilled in the art that impedance comprises a resistive component and a reactive component. The magnitude of the reactive component is indicated by a phase angle determined by measuring the time delay between the zero crossing of the measuring signal from the signal generator 30 applied to the first pair of electrodes 40, 41, and the zero crossing of the sine wave detected by the second pair of electrodes 45, 46.

Preferably, the system 10 is powered by the low voltage rechargeable power supply 17, including an 8 volt rechargeable battery (see FIG. 1. The highest internal working voltage in the system 10 is thus limited to 24 volts and the system 10 is isolated when the battery recharger 18 is connected thereto. There is no known risk to a subject exposed to voltages and currents having the above-stated magnitudes in this frequency range.

In experiments performed by other researchers, it was determined that the body's resistance was comprised of a resistance factor and a capacitance factor, and that it had no appreciable inductive impedance. However, in accordance with the present invention, the capacitive component is produced by the cell membranes and the water in the cells, and this intracellular compartment forms the primary frequency dependent impedance component. The extracellular water is indicated by a resistive component and the intracellular compartment also contributes a resistive component.

The equations employed in determining body water compartmentalization are discussed below. By way of introduction, if a human body is incorporated in an alternating current electrical circuit, the effect on the impedance of the circuit is very close to what would be expected if the body were composed of a resistor in parallel with a resistor and capacitor. If we denote a resistor and capacitor in series as $R_i$ and $C_i$ and a resistor in parallel with these as $R_e$, then the impedance of the resulting circuit, Z, is $Z=R_e \{(R_i^2+X_c^2)/[(R_e+R_i)^2+X_c^2]\}^{0.5}$ [equation (1)], where $X_c$ is reactive capacitance which equals $1/(2\pi fC_i)$ where f is the frequency of the alternating current.

It is assumed that the cells in the human body have a capacitive as well as a resistive component while the extracellular fluid acts solely as a resistor. Therefore, we would expect to see positive correlations between the volume of extracellular fluid and the extracellular resistance, $R_e$, between the intracellular resistance, $R_i$, and the intracellular fluid volume, and between the cellular capacitance, $C_i$, and intracellular fluid volume.

In order to estimate body water volumes, mathematical models were developed which expressed hypothesized relationships between the isotopically estimated body water volumes and the bioimpedance parameters, the concentration of sodium and potassium in serum, corrected for water content of serum, and the subject's anthropometric measurements.

The model for estimating extracellular water is described below. Assume that the extracellular water in the human body is a cylindrical resistor whose resistance, $R_E$, is $R_E=(K\,L)/A$ [equation (2)], where K is the conductivity constant of extracellular water, L is the length of the hypothetical cylinder occupied by the extracellular water, and A is the cross sectional area of the cylinder.

In order to examine the characteristics of K, the conductivity constant of extracellular water, an experiment was conducted in which the pairs of electrode 40, 41, 45, 46 were connected to either end of a resistor comprising a cylinder containing a solution of NaCl dissolved in water. The concentration of the NaCl was varied and the resistance was determined at a particular frequency for each concentration of NaCl. The length and cross sectional area of the resistor remained constant. Therefore, any changes in resistance were due to changes in the conductivity constant of the solution. In the range of concentrations viewed which would correspond to the range of ionic concentrations likely to be viewed in humans, the conductivity constant was shown to have the following form $K=K_2/I+K_3$ [equation (3)], where $K_2$ and $K_3$ are constants and I is the concentration of NaCl.

Substituting equation (3) into (2), multiplying the right side by L/L, and rearranging terms gives $V_E=K_2[L^2/(R_E I)]+K_3(L^2/R_E)$ [equation (4)], where $V_E=A^*L$, the volume of the hypothetical cylinder containing extracellular water. The form of equation (4) suggests that there is a linear relationship between the volume of a hypothetical cylindrical resistor containing extracellular water and $[L^2/(R_E I)]$ and $K_3(L^2/R_E)$. Therefore, a model similar to equation (4) and linear regression analysis was used to determine the least squares estimates of extracellular water. There were several considerations in specifying a linear regression model for extracellular water from equation (4). First, extracellular water in the human body is not precisely in the shape of a cylinder. Therefore, the subject's height was used as an estimate of L in (4). Second, it is not possible to directly measure the resistance, $R_E$, of the extracellular water. Therefore, we used $R_e$, from equation (1), as an estimate of RE. Third, since the total concentration of ions in extracellular water which would correspond to I was not measured directly, the sum of the concentrations of sodium and potassium ions in serum in millimoles per liter, corrected for the water content of serum, was used as an estimate of I. The following model is the result $V_e=b_0+b_1\,[H^2/(R_e M)]$, [equation (5)], where $V_e$ is the estimated extracellular water volume in liters, H is the subject's height in centimeters, M is the sum of the concentration of the subject's sodium and potassium ions in millimoles per liter, and $b_0$ and $b_1$ are the multivariate linear regression coefficients.

The model for estimating intracellular water is similar to that for extracellular water in that it contains components related to the resistance of the intracellular water, but it also contains a component that is related to the capacitance of cells. As the volume of intracellular water increases, the capacitance of the cells also increases. The derivation of the model is described below.

For the sake of simplicity, assume that there is a single cell in the human body, that it is spherical, and that it acts as a capacitor, such that the cell walls act as the plates of the capacitor. In general, the relationship between capacitance, $C_I$, the area of the plates of the capacitor, A, the distance between the plates, L, and the dielectric constant of the material between the plates, D, is given by $C_I=D(A/L)$ [equation (6)].

For the cell as a capacitor we assume that the plates of the capacitor are portions of the cell wall on opposite sides of the cell, the distance between the plates is the diameter of the cell, and the dielectric constant is proportional to the tonicity of the intracellular fluid. Therefore, equation (6) becomes $C_I=(K_4 I\,V_I)/L^2$ [equation (7)], where $K_4$ is a constant, I is the tonicity of the intracellular fluid, and $V_I$ is the volume of the cell.

Rearranging terms in equation (7) gives $V_I=(C_I L^2)/(k_4\,I)$ [equation (8)]. This suggests that there is a linear relationship between intracellular water volume and $(C_I L^2)/I$. In deriving a model for the volume of intracellular water from equation (8), the capacitance of the cells cannot be directly measured. Therefore, $C_i$ was used as an estimate of $C_I$. M, the sum of concentrations of sodium and potassium ions in serum, corrected for the water content of serum, was used as an estimate of I. Finally, a subject's height was used as an estimate of the diameter of our hypothetical single cell. These elements were combined with the intracellular water resistance components to give the following linear regression model $V_i=b_0+b_1\,(C_i H^2)/M+b_2\,H^2/(R_i M)$ [equation (9)], where $V_i$ is the estimated intracellular water volume in liters, H is the subject's height in centimeters, $R_i$ and $C_i$, from (1) are estimates of the resistance and capacitance associated with the intracellular water, M is the serum concentration of sodium plus potassium ions in millimoles per liter, and $b_0$, $b_1$, and $b_2$ are regression coefficients.

The model for total body water is a combination of the extracellular and intracellular water models: $V_t=b_0+b_1[H^2/(R_e M)]+b_2(C_i H^2)/M+b_3 H^2/(R_i M)$ [equation (10)], where $V_t$ is the estimated volume of total body water in liters and $b_0$, $b_1$, $b_2$, and $b_3$ are multivariate linear regression coefficients.

Linear multivariate regression analysis was employed with each of these three models to determine the regression coefficients which would produce the best least squares estimates of body water volumes. The isotopically estimated volumes of total body water, extracellular water, and intracellular water served as the criteria variables and the measurements described in equations (5), (9), and (10) were used as the predictor variables.

In operation, and with reference to FIGS. 1 and 2, the first pair of electrodes 40, 41 is typically placed on the side of the dominant hand and ipsalateral foot of the subject. The subject's skin is then cleansed with a suitable cleansing product and an electrolyte cream is applied to the electrode application points to ensure good electrical contact. The resistance measurement is effected through the second pair of electrodes 45, 46, which is disposed at the level of the radial styloid, and at a point between the maleoli of one of the ankles of the subject, respectively.

Anthropometric data relating to the subject, as well as weight data 80, are transmitted over the communications link 19 and entered into the microprocessor 31 by way of the keyboard 12 and/or electronic scale 13. Signals are applied to the subject at each of the frequencie for a predetermined period of time, typically on the order of 0.05 seconds. Impedance measurements were made at 1, 2, 5, 10, 20, 50, 100, 200, 500, 1000, and 2000 kilohertz for each subject. The signals generated by the instrumentation amplifiers 60, 61 are detected by the amplitude and phase detectors 63, 64, 65 and output signals therefrom are processed by the microprocessor 31. Bioelectrical impedance measurements, identifying data, electrolyte concentration data, and several anthropometric measurements are recorded for each subject. These may include several of the following: sex, height, weight, wrist circumference, elbow diameter, arm span, and an estimate of the current path which includes arm length, trunk length, and length of the leg. The above-described experimentally derived equations are then employed to compute the subject's body compartmentalization information. Data computed by the microprocessor 31 and control unit 11 are transmitted to the printer 14 and/or the display 15 for use by the physician.

Figure 3:
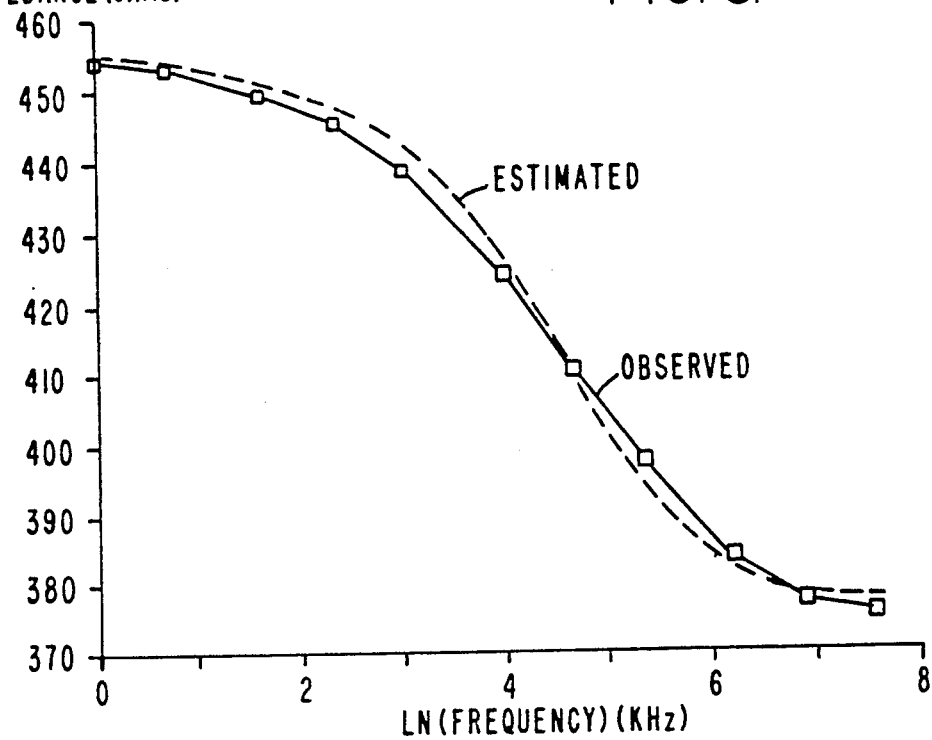
FIG. 3 is a graph illustrating the observed and estimated impedance of a typical subject measured using the system of FIG. 1.
Figure 4:
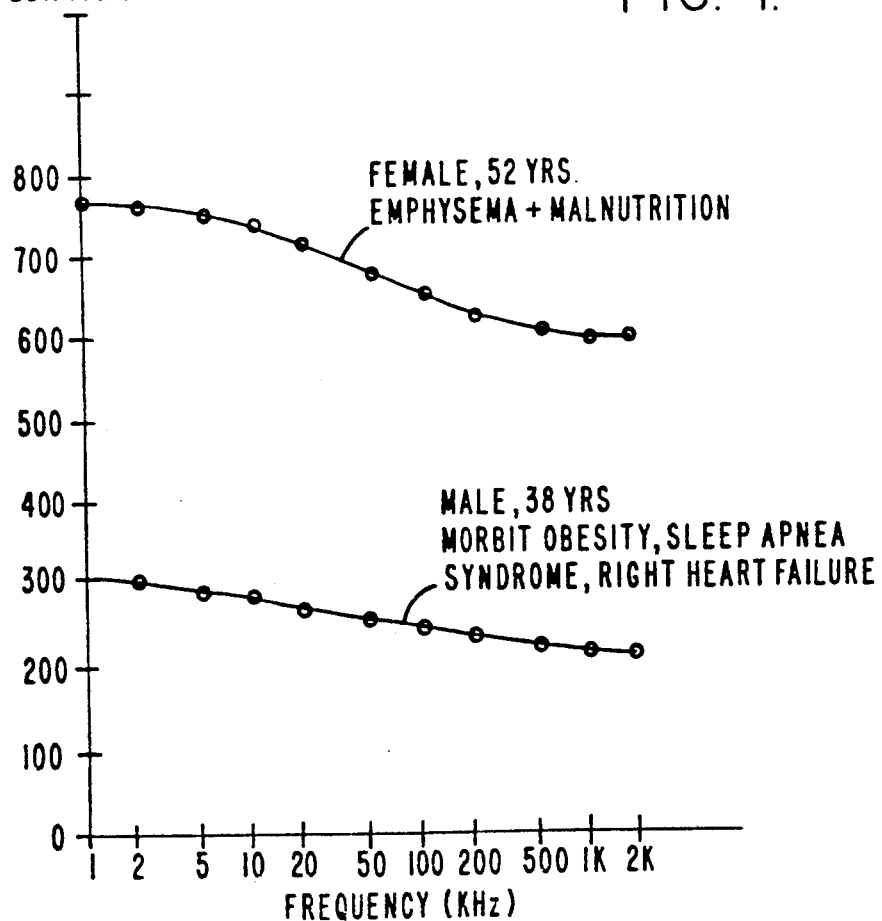
FIG. 4 is a graph showing impedance versus frequency measurements taken with the system made in accordance with the present invention utilizing two patients having known diseases.

A typical set of bioimpedance readings is presented in FIG. 3. It is clear that the measured impedance varies with frequency. This suggests that when the human body is considered as an electrical circuit, it has a capacitive as well as a resistive element. The shape of the graph depicting the bioimpedance measurements in FIG. 3 is consistent with those which would be obtained by measuring an electrical circuit having a resistor in parallel with a resistor and capacitor. Typical bioimpedance data for two subjects suffering from morbid obesity and emphysema are shown in FIG. 4. This data was derived using the system 10 of FIG. 1. The variation in body water compartmentalization as a result of these diseases is reflected in the differences in the two curves.

The data processing algorithms employed in the microprocessor 31 are described below. The estimates of extracellular resistance, $R_e$ and intracellular resistance, $R_i$, and capacitance, $C_i$ are calculated using an iterative technique based on a method developed by Marquardt and described by Press, et al. The initial estimates of $R_e$, $R_i$, and $C_i$ are calculated using linear combinations of the measured impedance readings. The form of these linear combinations was derived from the above-described experimental data. The accuracy of the initial estimates is important since it is a critical factor in determining the number of iterations required to achieve a desired degree of convergence. The test of the adequacy of convergence in the estimation technique was also derived from experimental data. It provides a sufficient degree of accuracy without requiring excessive iterations.

Once $R_e$, $R_i$, and $C_i$ have been estimated, the models described above are used to estimate volumes of total body water, extracellular water, and intracellular water. The parameters of the models have been determined based on experimental data. For each subject, the volumes of total body water, extracellular water, and intracellular water were estimated using isotope dilution methods. Also, anthropometric measurements, electrolytic concentration measurements and bioelectrical impedance at several frequencies was collected for each subject.

Within the experimental error of the isotope dilution technique, use of the bioimpedance measuring system 10 of the present invention provides for an accurate predictor of intercellular water, extracellular water and total body water.

It should be apparent that the system 10 described herein provides for the accurate measurement of factors indicative of a subject's frequency dependent body impedance. This information and algorithms from empirical data analysis including anthropometric measurements, electrolyte concentration, and isotopic determination of body water compartments allow prediction of total body water, intracellular water and extracellular water without the need to use isotopes.

From the above description, it should be apparent that the present invention provides an automatic, accurate, and repeatable apparatus for measuring body water volumes of a subject and specifically for determining composition or compartmentalization of body water between intracellular and extracellular water. The present invention provides a simple, reliable, and noninvasive means for monitoring these significant parameters, thereby significantly enhancing a physician's ability to treat his patients.

Thus there has been described a new and improved apparatus for monitoring body water compartmentalization. It is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. Apparatus for measuring the body water compartmentalization of a human subject, having potassium ion and sodium ion concentrations which can be used to form a sum, comprising:

means for generating alternating constant current signals at a plurality of predetermined frequencies, and for coupling the alternating constant current signals to a human subject between two selected physical locations thereon;

measuring means coupled to two selected different locations on the subject for determining resistance, phase angle and impedance data associated with the subject at each of the plurality of predetermined frequencies;

data generation means for generating a plurality of signals comprising electrolytic concentration and anthropometric data associated with the subject; and processor means connected to the data generation means and measuring means for processing the resistance, phase angle, electrolytic concentration and anthropometric data, and for computing intracellular, extracellular and total water volumes of the subject as a function thereof in accordance with predefined equations having a form $V_e = b_0 + b_1[H^2/(R_e M)]$, $V_i = b_0 + b_1(C_i H^2)/M + b_2 H^2/(R_i M)$, and $V_t = b_0 + b_1[H^2/(R_e M)] + b_2(C_i H^2)/M + b_3 H^2/(R_i M)$ for intracellular, extracellular and total body water volumes, respectively, and where H is the subject's height, M is the sum of the concentration of the subject's sodium and potassium ions, and $b_0$, $b_1$, $b_2$, and $b_3$ are predetermined multivariate linear regression coefficients.

2. The apparatus of claim 1 wherein the means for generating alternating constant current signals includes a means for generating sequence of alternating current signals generates which signals at different predetermined frequencies in a range from 1 kHz to 1 MHz.

3. The apparatus of claim 2 wherein the means for generating a sequence of alternating constant current signals includes a first pair of electrodes for applying the alternating constant current signals to the subject, and wherein the measuring means includes a second pair of electrodes for measuring a voltage drop and phase shift of the constant current signals, the measuring means including circuit means for generating direct current signals in response to the voltage drop of the alternating constant current signals, and phase shift measuring means for generating direct current signals in response to the voltage drop and phase shift, and wherein the measuring means is located physically proximate to the pairs of electrodes.

4. The apparatus of claim 3 wherein the measuring means further comprises active electrode pairs that incorporate at least one amplifier coupled to selected electrodes of each electrode pair, which amplifier is substantially colocated at the electrode pair.

5. Apparatus for measuring body water compartmentalization of a human subject, having potassium ion and sodium ion concentrations which can be used to form a sum, comprising:

signal generating means for generating a sequence of alternating current electrical signals having a predetermined constant current, each signal of the sequence having a different predetermined frequency;

means for applying the sequence of signals across a first predetermined pair of locations on the subject;

measuring means coupled to the subject for determining body resistance between a second pair of locations disposed between the first pair of locations on the subject, and for generating a resistance signal and measuring means for determining a phase angle between the applied alternating current signals and voltage signals measured at the second pair of locations and generating a phase shift signal;

data generation means for generating and storing anthropometric and electrolyte concentration data related to the subject;

processor means coupled to the measuring means for processing the body resistance and phase angle data, and coupled to the data generation means for processing the anthropometric and electrolyte concentration data to compute extracellular, intracellular and total water volumes of the subject in accordance with predetermined relationships having a form $V_e = b_0 + b_1[H^2/(R_e M)]$, $V_i = b_0 + b_1(C_i H^2)/M + b_2 H^2/(R_i M)$, and $V_t = b_0 + b_1[H^2/(R_e M)] + b_2(C_i H^2)/M + b_3 H^2/(R_i M)$ for intracellular, extracellular and total body water volumes, respectively, and where H is the subject's height, M is the sum of the concentration of the subject's sodium and potassium ions, and $b_0$, $b_1$, $b_2$, and $b_3$ are predetermined multivariate linear regression coefficients; and display means coupled to the processor means for displaying the computed intracellular, extracellular and total water volumes of the subject.

6. The apparatus of claim 5 further comprising current monitoring means for monitoring a magnitude of the current applied to the subject and regulator means connected to the current monitoring means for regulating an output of a power amplifier in response thereto.

7. The apparatus of claim 6 wherein the current monitoring means includes an amplitude detector for measuring an amplitude of the monitored current and for comparing the monitored current to a reference signal, and integrating means connected to the amplitude detector for integrating an output thereof to produce a feedback signal.

8. The apparatus of claim 5 wherein said means for applying the sequence of signals includes a first pair of electrodes coupled to a first predetermined pair of points on the subject.

9. The apparatus of claim 7 wherein the measuring means comprises a phase detector circuit, and wherein a computing circuit includes means for computing an impedance between the second predetermined pair of points at each frequency as a function of resistance and phase shift.

10. The apparatus of claim 9 wherein the processor means comprises a microprocessor having a multiplexer coupled to the current monitoring means, the resistance measuring means and phase shift measuring means, said multiplexer comprising means for coupling current, resistance and phase shift signals to the microprocessor for computation.

11. The apparatus of claim 10 further including an isolation amplifier connected between the current monitoring means and one of the first pair of locations, and between the resistance measuring means and second one of the pair of locations.

12. The apparatus of claim 11 further including an analog-to-digital converter coupled between an output of the multiplexer and the microprocessor for converting measured resistance, current, and phase shift signals into digital signals.

13. The apparatus of claim 12 wherein the anthropometric parameters include total body weight of the subject and distances between the first and second pairs of points, and wherein the means for generating and storing the anthropometric data includes a keyboard and scale.

14. The apparatus of claim 13 further including means for inputting a plurality of scaling factors into the microprocessor, and wherein the microprocessor includes means for outputting scaled values of intracellular and extracellular and total body water volume as a function thereof.

15. The apparatus of claim 14 further including display means for displaying the scaled value of the extracellular and intracellular body water volumes.

16. The apparatus of claim 15 further including isolation amplifiers connected between selected ones of each of the locations of the first and second pairs of locations and the resistance, current, and phase shift measuring means.

17. The apparatus of claim 4 wherein the measuring means comprises active electrodes which imcorporate at least one amplifier coupled to each electrode pair.

18. Apparatus for measuring the body water compartmentalization of a human subject, comprising:

signal generating means for generating a sequence of alternating current, constant current electrical signals at a predetermined number of different frequencies;

means for applying the sequence of constant current electrical signals across a first predetermined pair of points on the subject;

means for sensing the sequence of alternating current, constant current electrical signals applied to the subject;

means for sensing an electrical current at a second predetermined pair of points on the subject, which sensed current is proportional to resistance between the second pair of points;

means for measuring and electronically storing anthropometric and electrolyte concentration data of the subject; and processor means for processing sensed constant current and sensed electrical signals derived from the first and second pairs of electrodes and the anthropometric and electrolyte concentration data in accordance with predetermined relationships having a form $V_e = b_0 + b_1[H^2/(R_eM)]$, $V_i = b_0 + b_1(C_iH^2)/M + b_2H^2/(R_iM)$, and $V_t = b_0 + b_1[H^2/R_eM)] + b_2(C_iH^2)/M + b_3H^2/(R_iM)$ for entracellular, extracellular and total body water volumes, respectively, and where H is the subject's height, M is the sum of the concentration of the subject's sodium and potassium ions, and $b_0$, $b_1$, $b_2$ and $b_3$ are predetermined multivariate linear regression coefficients to compute intracellular, extracellular and total water volumes of the subject as a function thereof.

19. Apparatus for determining body water compartmentalization of a human subject utilizing anthropometric data of the subject, said apparatus comprising:

signal generating means for selectively generating a plurality of alternating constant current signals that each have a different predetermined frequency;

first and second electrodes disposed on the subject and adapted to couple the alternating constant current signals to the subject;

third and fourth electrodes disposed on the subject at selected locations between the first and second electrodes and comprising means for coupling the alternating constant current signals applied to the subject;

processing means coupled to the second, third, and fourth electrodes and electrical ground, for processing the signals coupled thereby including means for generating a first amplitude signal indicative of the amplitude of the signal sensed between the second and third electrodes, and means for generating a second amplitude signal indicative of the amplitude of the signal sensed between the fourth electrode and electrical ground, and means for generation a phase signal indicative of a phase difference between the first and second amplitude signals; and microprocessor means for containing stored anthropometric data relating to the subject coupled to the processing means, for processing the first and second amplitude signals, the phase signals, and the anthropometric data to compute body water compartmentalization of the subject in accordance with predetermined relationships having a form $V_e = b_0 + b_1 [H^2/(R_eM)]$, $V_i = b_0 + b_1 (C_iH^2)/M - H^2/(R_iM)$, and $V_t = b_0 + b_1 [(H^2/R_eM)] + b_3 (C_i H^2)/M + b_3 H^2/(R_iM)$ for intracellular, extracellular and total body water volumes, respectively, and where H is the subject's height, M is the sum of the concentration of the subject's sodium and potassium ions and $b_0$, $b_1$, $b_2$, and $b_3$ are predetermined multivariate linear regression coefficients.

20. A method of determining the body water compartmentalization of a human subject utilizing anthropometric data of the subject, said method comprising the steps of:

generating alternating constant current signals at a plurality of different predetermined frequencies;

coupling the alternating constant current signals to a first plurality of locations on the subject;

sensing the alternating constant current signals applied to the subject;

sensing the phase angle between constant current signals and signals derived at a second plurality of locations on the subject located between the first plurality of locations;

processing the sensed signals to generate a first amplitude signal indicative of an amplitude of a signal sensed between a first plurality of locations, and to generate a second amplitude signal indicative of an amplitude of a signal sensed between the second pluarlity of locations, and to generate a phase signal indicative of a phase difference between the first and second amplitude signals; and processing the first and second amplitude signals, the phase signals, and the anthropometric data of the subject to compute body water compartmentalization of the subject in accordance with predetermined relationships having a form $V_e = b_0 + b_1 [H^2/(R_eM)]$, $V_i = b_0 + b_1 (C_iH^2)/M + b_2H^2/(R_iM)$, and $V_t = b_0 + b_1[H^2/(R_eM)] + b_2 (C_iH^2)/M + b_3H^2/(R_iM)$ for intracellular, extracellular and total body water volumes, respectively, and where H is the subject's height, M is the sum of the concentration of the subject's sodium and potassium ions, and $b_0$, $b_1$, $b_2$, and $b_3$ are predetermined multivariate linear regression coefficients, and $b_0$, $b_1$, $b_2$, and $b_3$ are predetermined multivariate linear regression coefficients to compute intracellular, extracellular and total water volumes of the subject as a function thereof.

21. A method of determining body water compartmentalization of a subject, said method comprising the steps of:

generating alternating constant current signals at a plurality of different predetermined frequencies;

coupling the alternating constant current signals to a plurality of locations on the subject;

sensing the alternating constant current signals applied to the subject at a second plurality of selected locations;

processing selected ones of the sensed signals to generate a first amplitude signal indicative of an amplitude of a signal sensed between a first set of locations, and to generate a second amplitude signal indicative of an amplitude of a signal sensed between a second set of locations, and to generate a phase signal indicative of a phase difference between the first and second amplitude signals;

processing the first and second amplitude signals, the phase signals, and anthropometric data of the subject to compute a body impedance of the subject as a function of frequency; and processing the first and second amplitude signals, the phase signals, and the anthropometric data related the subject to compute the body water compartmentalization of the subject in accordance with predetermined relationships having a form $V_e = b_0 + b_1 [H^2/(R_e M)]$, $V_i = b_0 + b_1 (C_i H^2)/M + b_2 H^2/(R_i M)$, and $V_t = b_0 + b_1 [H^2/(R_e M)] + b_2 (C_i H^2)/M + b_3 H^2/(R_i M)$ for intracellular, extracellular and total body water volumes, respectively, and where H is the subject's height, M is the sum of the concentration of the subject's sodium and potassium ions, and $b_0$, $b_1$, $b_2$, and $b_3$ are predetermined multivariate linear regression coefficients to compute intracellular, extracellular and total water volumes of the subject as a function thereof.

* * * * *